(12) United States Patent
Chang et al.

(10) Patent No.: US 9,340,794 B2
(45) Date of Patent: May 17, 2016

(54) METHOD FOR ORDERING AND INTRODUCING MULTIPLE GENES INTO A GENOME

(75) Inventors: Jui-Jen Chang, Kaohsiung (TW); Feng-Ju Ho, Pingtung (TW); Cheng-Yu Ho, Bade (TW); Wen-Hsiung Li, Yuanshan Township (TW); Ming-Che Shih, Taipei (TW); Chieh-Chen Huang, Taichung (TW)

(73) Assignee: Academia Sinica, Taipei (TW)

( * ) Notice: Subject to any disclaimer, the term of this patent is extended or adjusted under 35 U.S.C. 154(b) by 671 days.

(21) Appl. No.: 13/601,146

(22) Filed: Aug. 31, 2012

(65) Prior Publication Data

US 2014/0248703 A1 Sep. 4, 2014

Related U.S. Application Data

(60) Provisional application No. 61/529,360, filed on Aug. 31, 2011.

(51) Int. Cl.
*C12N 15/66* (2006.01)
*C12N 15/81* (2006.01)

(52) U.S. Cl.
CPC .................................. *C12N 15/815* (2013.01)

(58) Field of Classification Search
None
See application file for complete search history.

(56) References Cited

U.S. PATENT DOCUMENTS

| | | | |
|---|---|---|---|
| 5,625,126 A * | 4/1997 | Lonberg et al. | 800/18 |
| 8,198,089 B2 * | 6/2012 | Akada et al. | 435/471 |
| 2002/0028444 A1 * | 3/2002 | Harney et al. | 435/6 |
| 2008/0293101 A1 * | 11/2008 | Peters et al. | 435/69.1 |

OTHER PUBLICATIONS

Bitinaite et, al., "USER™ friendly DNA engineering and cloning method by uracil excision", 2007, Nucleic Acids Res 35: 1992-2002.
Gibson et al., "Enzymatic assembly of DNA molecules up to several hundred kilobases", 2009, Nat Methods 6:341-345.
Gibson et al., "One-step assembly in yeast of 25 overlapping DNA fragments to form a complete synthetic *Mycoplasma genitalium* genome", 2008, Proc Natl Acad Sci 105(51):20404-9.
Klock et al., "Combining the polymerase incomplete primer extension method for cloning and mutagenesis with microscreening to accelerate structural genomics efforts", 2008, Proteins 71: 982-994.
Li and Elledge, "Harnessing homologous recombination in vitro to generate recombinant DNA via SLIC", 2007, Nat Methods 4: 251-256.
Li and Elledge, "MAGIC, an in vivo genetic method for the rapid construction of recombinant DNA molecules", 2005, Nat Genet 37: 311-319.
Marsischky and Labaer, "Many Paths to Many Clones: A Comparative Look at High-Throughput Cloning Methods", 2004, Genome Res 14: 2020-2028.
Pachuk et al., "Chain reaction cloning: a one-step method for directional ligation of multiple DNA fragments", 2000, Gene 243:19-25.
Quan and Tian, "Circular Polymerase Extension Cloning of Complex Gene Libraries and Pathways", 2009 PLOS-One 4:6.
Shao et al., "DNA assembler, an in vivo genetic method for rapid construction of biochemical pathways", 2009, Nucleic Acid Res 37:2.
Tsuge et al., "One step assembly of multiple DNA fragments with a designed order and orientation in *Bacillus subtilis* plasmid", 2003, Nucleic Acid Res 31:8.

* cited by examiner

*Primary Examiner* — Jim Ketter
(74) *Attorney, Agent, or Firm* — Cesari and McKenna LLP

(57) ABSTRACT

Described is a method of introducing multiple nucleic acid molecules into the genome of a cell. The method includes providing a plurality of nucleic acid molecules, each of the plurality of nucleic acid molecules containing (a) a nucleic acid sequence operatively linked to a promoter sequence at the 5' end of the nucleic acid molecule, and (b) an overlapping sequence at the 3' end of the nucleic acid molecule.

17 Claims, 7 Drawing Sheets

SEQUENCE LISTING

<160> NUMBER OF SEQ ID NOS: 40

<210> SEQ ID NO 1
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 1
tagggcctgt ttggcctccc gcggggatc                              29

<210> SEQ ID NO 2
<211> LENGTH: 80
<212> TYPE: DNA
<213> ORGANISM: Artificial Sequence
<220> FEATURE:
<223> OTHER INFORMATION: Synthetic oligonucleotide

<400> SEQUENCE: 2
tagcactcag tgattattta cgtattcttt gaaatggcag tattgataat gataaactta    60
tacaacatcg aagaagagtc                                                80

<210> SEQ ID NO 3
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 3
taggccatga cggcagttta tcattatcaa tactgcc                     37

<210> SEQ ID NO 4
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 4
gtagagaatt tcattttttt gtttgtttat gtgtgtttat                  40

<210> SEQ ID NO 5
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 5
ataaacacac ataaacaaac aaaaaaatga aattctctac                  40

<210> SEQ ID NO 6
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 6
aagatttaaa gtaaattcac gcggccgcct actttcttgc gagacacg         48

<210> SEQ ID NO 7
<211> LENGTH: 48

-continued

<212> TYPE: DNA
<213> ORGANISM: Artificial Sequence
<220> FEATURE:
<223> OTHER INFORMATION: Synthetic oligonucleotide

<400> SEQUENCE: 7
cgtgtctcgc aagaaagtag gcggccgcgt gaatttactt taaatctt                48

<210> SEQ ID NO 8
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 8
agtatggtaa cgaccgtaca ggcaa                                          25

<210> SEQ ID NO 9
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 9
gtagagaatt catttttttt tgtgtaatat tcttttttt                           40

<210> SEQ ID NO 10
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 10
aaaaaaaaga atattacaca aaaaaaatga aattctctac                          40

<210> SEQ ID NO 11
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 11
aagatttaaa gtaaattcac gcggccgctt acaggcactg agagtagt                 48

<210> SEQ ID NO 12
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 12
actactctca gtgcctgtaa gcggccgcgt gaatttactt taaatctt                 48

<210> SEQ ID NO 13
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 13

```
tggtaacgac cgtacaggca agcgcgaagg caaatggaaa agctggtggc ggaaaaaatt    60
catttg                                                               66

<210> SEQ ID NO 14
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 14
ccagcttttc catttgcctt cgcgcttgcc                                     30

<210> SEQ ID NO 15
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 15
tcctcgccct tgctcaccat tttatctttt tttagtatag agt                      43

<210> SEQ ID NO 16
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 16
actctatact aaaaaaagat aaaatggtga gcaagggcga gga                      43

<210> SEQ ID NO 17
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 17
taggccgtcg tggcatgtat gggtttggtt gccagaaaag aggaagtcca tattgtacac    60

<210> SEQ ID NO 18
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 18
taggccacga cggcgtgtac aatatggact tcctcttttc                          40

<210> SEQ ID NO 19
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 19
acgagatcta aaaaaatgaa attctct                                        27

<210> SEQ ID NO 20
<211> LENGTH: 27
```

<210> SEQ ID NO 20
<211> LENGTH: 27 (implied)
<212> TYPE: DNA
<213> ORGANISM: Artificial Sequence
<220> FEATURE:
<223> OTHER INFORMATION: Synthetic oligonucleotide

<400> SEQUENCE: 20
tatcccgggt tagtaaagtt tgtaagc                                    27

<210> SEQ ID NO 21
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 21
agggccaaga aggccagccg cggaaattta ggaattttaa ac                    42

<210> SEQ ID NO 22
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 22
taggccacga cggcgtgtac aatatggact tcctcttttc                       40

<210> SEQ ID NO 23
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 23
aaaaagatct gccaccatgg gtaaggaaaa gactc                            35

<210> SEQ ID NO 24
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 24
aaaaatctag attagaaaaa ctcatcgagc at                               32

<210> SEQ ID NO 25
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 25
gacatgtgcc agcaaatcca atatc                                      25

<210> SEQ ID NO 26
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 26

-continued

```
cttttccatt tgccttcgcg cttgcctgta cggtcgttac catacttggc ggaaaaaatt    60
catttg                                                              66

<210> SEQ ID NO 27
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 27
agtatggtaa cgaccgtaca ggcaa                                         25

<210> SEQ ID NO 28
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 28
aagtgttgcc atcgtagcag ttcgt                                         25

<210> SEQ ID NO 29
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 29
acgagatcta tggtgagcaa gggcga                                        26

<210> SEQ ID NO 30
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 30
tatcccgggt tacttgtaca gctcgtcca                                     29

<210> SEQ ID NO 31
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 31
tccaggtcca gttaatgttc cattc                                         25

<210> SEQ ID NO 32
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 32
tatcccgggt tagtaaagtt tgtaagc                                       27

<210> SEQ ID NO 33
<211> LENGTH: 25
```

```
<212> TYPE: DNA
<213> ORGANISM: Artificial Sequence
<220> FEATURE:
<223> OTHER INFORMATION: Synthetic oligonucleotide

<400> SEQUENCE: 33
caggatcttg ccatcctatg gaact                                              25

<210> SEQ ID NO 34
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 34
tacttggaaa tgctcgtgga atcaa                                              25

<210> SEQ ID NO 35
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 35
gacatgtgcc agcaaatcca atatc                                              25

<210> SEQ ID NO 36
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 36
aagtgttgcc atcgtagcag ttcgt                                              25

<210> SEQ ID NO 37
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 37
cgatctgaag ttcatcaatg gccag                                              25

<210> SEQ ID NO 38
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 38
gtgcagatga acttcagggt cagct                                              25

<210> SEQ ID NO 39
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 39
```

```
gaacttcaag atccgccaca acatc                                               25

<210> SEQ ID NO 40
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 40
cacattcacc aacatagaat ggatc                                               25
```

METHOD FOR ORDERING AND INTRODUCING MULTIPLE GENES INTO A GENOME

CROSS REFERENCE TO RELATED APPLICATION

This application claims priority to U.S. Provisional Application No. 61/529,360, filed on Aug. 31, 2011, the content of which is hereby incorporated herein in its entirety.

BACKGROUND

Synthetic biology is a new approach for design and construction of new biological systems, and for re-design of natural biological systems. To pursue large-scale genomic engineering of a cell, an efficient high-throughput method that can simultaneously introduce many genes into a genome is required.

Various techniques have been developed to enable the assembly of several genes or DNA modules into larger constructs, such as chain reaction cloning (Pachuk et al., 2000, Gene 243:19-25), ordered gene assembly in *Bacillus subtilis* (OGAB) (Tsuge et al., 2003, Nucleic Acid Res 31:8), DNA assembler in vivo (Shao et al., 2004, Nucleic Acid Res 37:10), uracil-specific excision reagent (USER) cloning (Bitinaite et, al., 2007, Nucleic Acids Res 35: 1992-2002), mating-assisted genetically integrated cloning (MAGIC) (Li and Elledge, 2005, Nat Genet 37: 311-319), sequence- and ligation-independent cloning (SLIC) (Li and Elledge, 2007, Nat Methods 4: 251-256), In-Fusion (Clontech; Marsischky and LaBaer, 2004, Genome Res 14: 2020-2028), polymerase incomplete primer extension (PIPE) (Klock et al., 2008, Proteins 71: 982-994), circular polymerase extension cloning (Quan and Tian, 2009 PLOS-One 4:6), and one-step assembly in yeast (Gibson et al., 2008, Proc Natl Acad Sci 105(51):20404-9; Gibson et al., 2009, Nat Methods 6:341-345). These methodologies are based mainly on historically well-characterized hosts, such as *Escherichia coli, Bacillus subtilis*, and *Saccharomyces cerevisiae*. Other less-studied organisms are still in need of molecular biological tools.

SUMMARY

This invention is based on the discovery of a method, i.e., Promoter-based Gene Assembly and Simultaneous Overexpression (PGASO), that can efficiently insert multiple gene cassettes in a predetermined order into a predetermined site of the genome of a cell. In particular, it was shown that this method can be applied to *Kluyveromyces marxianus*. PGASO is superior to current technologies for genome engineering for at least four reasons: (1) Multiple genes can be transformed into a genome in one single step; (2) Specific upstream promoter sequences are employed for gene assembly in a predesigned order without linker sequences; (3) Gene cassettes with individual promoters can be co-expressed at different expression levels; (4) PGASO is applicable to any host whose genome can be engineered via homologous recombination.

Accordingly, described herein is a method of inserting a plurality of nucleic acid molecules in a predetermined order into the genome of a cell. The method includes providing a plurality of nucleic acid molecules to be inserted into a predetermined site in the genome of a cell in a predetermined order next to each other, the plurality of nucleic acid molecules including a first nucleic acid molecule, a last nucleic acid molecule and at least one intervening nucleic acid molecule to be inserted between the first and last nucleic acid molecules. Each of the plurality of nucleic acid molecules contains (a) a nucleic acid sequence operably linked to a promoter sequence at the 5' end of the nucleic acid molecule, and (b) an overlapping sequence at the 3' end of the nucleic acid molecule, the promoter sequence in each nucleic acid molecule being different. The overlapping sequence in the at least one intervening nucleic acid molecule is homologous to a portion of a promoter sequence in an adjacent nucleic acid molecule and a portion of the promoter sequence in the at least one intervening nucleic acid molecule is homologous to the overlapping sequence in another adjacent nucleic acid molecule. A portion of the promoter sequence of the first nucleic acid molecule is homologous to a first sequence in the predetermined site and the overlapping sequence of the last nucleic acid molecule is homologous to a second sequence in the predetermined site. The plurality of nucleic acid molecules are introduced into the cell, whereby the plurality of nucleic acid molecules join together in the predetermined order via homologous recombination between the overlapping sequences and the promoter sequences, and are inserted into the genome via homologous recombination between the promoter sequence of the first nucleic acid molecule and the first sequence in the predetermined site and between the overlapping sequence of the last nucleic acid molecule and the second sequence in the predetermined site.

The above-described method can be used to engineer a cell for various purposes. For example, the method can be used to design a cell that has certain enzymatic activities. Thus, each of the plurality of nucleic acid molecules can include a nucleic acid sequence encoding an enzyme, e.g., a beta-glucosidase, an endoglucanase, an exoglucanase, a cellubiohyrolase, a protease, a nuclease, an amylase, a laccases, a pectinase, and a lipase.

Also contemplated herein are engineered *Kluyveromyces marxianus* cells that express heterologous proteins.

In one aspect, the engineered *Kluyveromyces marxianus* cell contains in its genome (1) a first nucleic acid molecule that contains the *K. lactis* Lac4 promoter operably linked to the KanMx gene, (2) a second nucleic acid molecule that contains the *S. cerevisiae* GapDHI promoter operably linked to the *T. reesei* egIII gene, (3) a third nucleic acid molecule that contains the *K. lactis* GapDHI promoter operably linked to the *T. reesei* cbhI gene, (4) a fourth nucleic acid molecule that contains the *K. lactis* AdhI promoter operably linked to the green florescent protein gene, and (5) a fifth nucleic acid molecule that contains the *S. cerevisiae* AdhI promoter operably linked to the *N. patriciarum* npabgs gene, (1)-(5) being adjacent to each other in the order of (1)-(2)-(3)-(4)-(5) in the 5' to 3' direction. The engineered cell expresses all of the proteins encoded by the genes of (1)-(5).

In another aspect, an engineered *Kluyveromyces marxianus* cell can contain in its genome (1) a first nucleic acid molecule that contains the *K. lactis* Lac4 promoter operably linked to the *A. niger* eglA-12 gene, (2) a second nucleic acid molecule that contains the *S. cerevisiae* GapDHI promoter operably linked to the *T. reesei* egIII gene, (3) a third nucleic acid molecule that contains the *S. cerevisiae* PGK promoter operably linked to the *A. niger* eglA-2 gene, (4) a fourth nucleic acid molecule that contains the *K. lactis* GapDHI promoter operably linked to the KanMx gene, (5) a fifth nucleic acid molecule that contains the *K. lactis* PGK promoter operably linked to the *T. reesei* cbhII gene, (6) a sixth nucleic acid molecule that contains the *K. lactis* AdhI promoter operably linked to the *T. reesei* cbhI gene, and (7) a seventh nucleic acid molecule that contains the *S. cerevisiae* AdhI promoter operably linked to the *N. patriciarum* npabgs gene, (1)-(7) being adjacent to each other in the order of (1)-(2)-(3)-(4)-(5)-(6)-(7) in the 5' to 3' direction. The engineered cell expresses all of the proteins encoded by the genes of (1)-(7).

The details of one or more embodiments of the invention are set forth in the accompanying drawing and the description below. Other features, objects, and advantages of the invention will be apparent from the description and drawing, and from the claims.

DETAILED DESCRIPTION

Figure 1A:
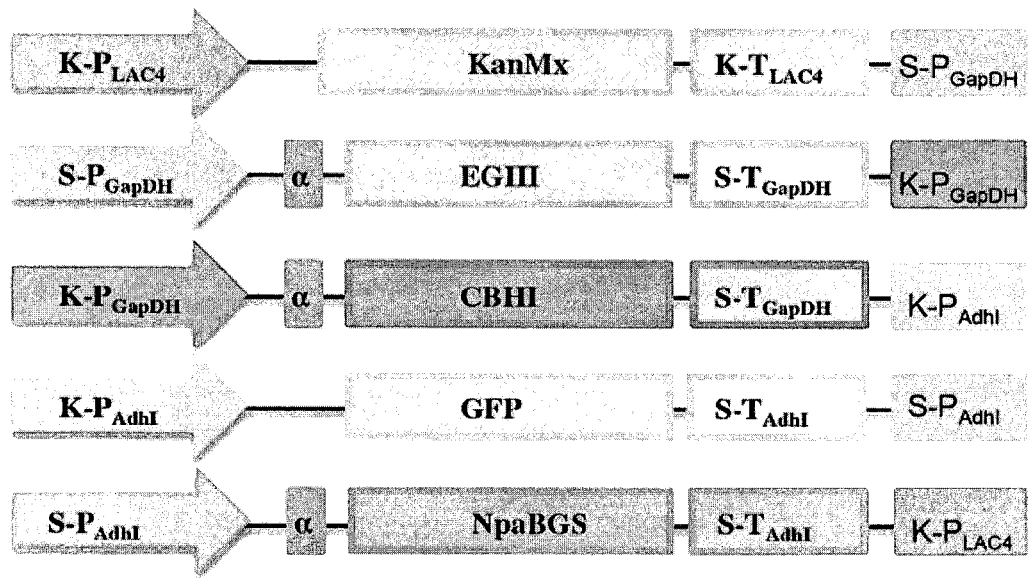
FIGS. 1(a) and (b) are schematic diagrams showing exemplary gene cassettes and the genomic integration of 5 gene cassettes in strain KR5.

Described herein is a method, i.e., PGASO, for inserting multiple nucleic acid molecules, e.g., gene cassettes, into the genome of a cell in a predetermined order, with a first nucleic acid molecule, a last nucleic acid molecule, and at least one intervening nucleic acid molecule between them. Each nucleic acid molecule contains at least 3 components: (1) a promoter sequence, (2) a gene sequence linked operably at the 5' end to the promoter sequence, and (3) an overlapping sequence at the 3' end of the nucleic acid molecule. See, FIG. 1(a).

A portion of the 5' end of the promoter sequence of the first nucleic acid molecule and a portion of the 3' end of the last nucleic acid molecule are homologous to sequences in a predetermined site in the host genome in order to facilitate site-specific insertion. Each promoter sequence of a nucleic acid molecule is different from the promoter sequences of the other nucleic acid molecules. The overlapping sequence is homologous to a portion of the promoter sequence in the adjacent downstream nucleic acid molecule.

When the nucleic acid molecules are introduced into a cell, they join together in the predesigned order via homologous recombination between the pairs of overlapping and promoter sequences. The joined nucleic acid molecules are inserted into the genome via homologous recombination between a portion of a predetermined genomic site and the promoter sequence of the first nucleic acid molecule, and between another portion of the predetermined genomic site and the 3' overlapping of the last nucleic acid molecule.

PSOGA can be applied, for example, in K. marxianus for designing optimal enzyme combinations or construction of desired pathways.

The promoter sequence is a nucleic acid sequence that includes a functional promoter. It can also include additional sequences, e.g., an endogenous 5' upstream sequence of the promoter or a sequence heterologous to the promoter. Preferably, the promoter sequence is at or near the 5' end of the nucleic acid molecule. Any suitable promoter can be used to construct the nucleic acid molecules described herein. Suitable promoters include the K. lactis Lac4 promoter, the S. cerevisiae GapDHI promoter, the K. lactis GapDHI promoter, the S. cerevisiae AdhI promoter, the K. lactis AdhI promoter, the S. cerevisiae PGK promoter, and the K. lactis PGK promoter. The 5' portions of the promoter sequences preferably do not share significant sequence identity with each other.

In previous studies, a number of promoters have been developed for gene expression systems in S. cerevisiae, but very few have been investigated in K. marxianus. The wide spectrum of driving strengths observed for different promoters in K. marxianus can be further utilized for constructing optimal enzyme combinations or regulating gene expression.

The overlapping sequence can be of any length sufficient to promote homologous recombination, e.g., between 40 and 2000 bases. It is preferably positioned at or near the 3' end of the nucleic acid molecule.

The predetermined site can be anywhere within the genome of a host cell. It can be within a promoter region in the genome. The site can also be a region including sequence repeats. It can also be an exogenous sequence inserted into the genome.

To monitor integration of the nucleic acid molecules into the genome, one of the nucleic acid molecule can include a sequence encoding a selectable marker (e.g., a protein conferring resistance to an antibiotic), and another can include a sequence encoding a reporter protein (e.g., green fluorescent protein). A skilled practitioner would be able to choose suitable selectable markers and reporter proteins.

The method described herein can be applied to any host cell. In particular, it can be used to efficiently engineer Kluyveromyces marxianus to express heterologous cellulytic enzymes, as shown in the examples describe below.

Data described below also suggest that the order of the genes and the strength of the promoter linked to a particular gene can be important factors in the formulation of a cellulase cocktail. The order of the genes and the promoter used to drive each gene can be designed such that the enzymes encoded by the genes are expressed in a particular ratio, e.g., more of one specific enzyme than another. Consequently, by changing the order of the genes and matching promoters to genes, the level ratio of the encoded enzymes can be optimized to achieve specific enzymatic activity or specificity.

The PGASO method is a very efficient way to integrate any number of gene cassettes in tandem into the genome of a cell, and to position the gene cassettes in a specific order to achieve a desired expression profile and a specific functional outcome.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are incorporated herein by reference in their entirety.

Example 1

Insertion of Five Gene Cassettes

Materials and Methods

(1) Multiple-Gene Cassette Construction

Figure 1B:
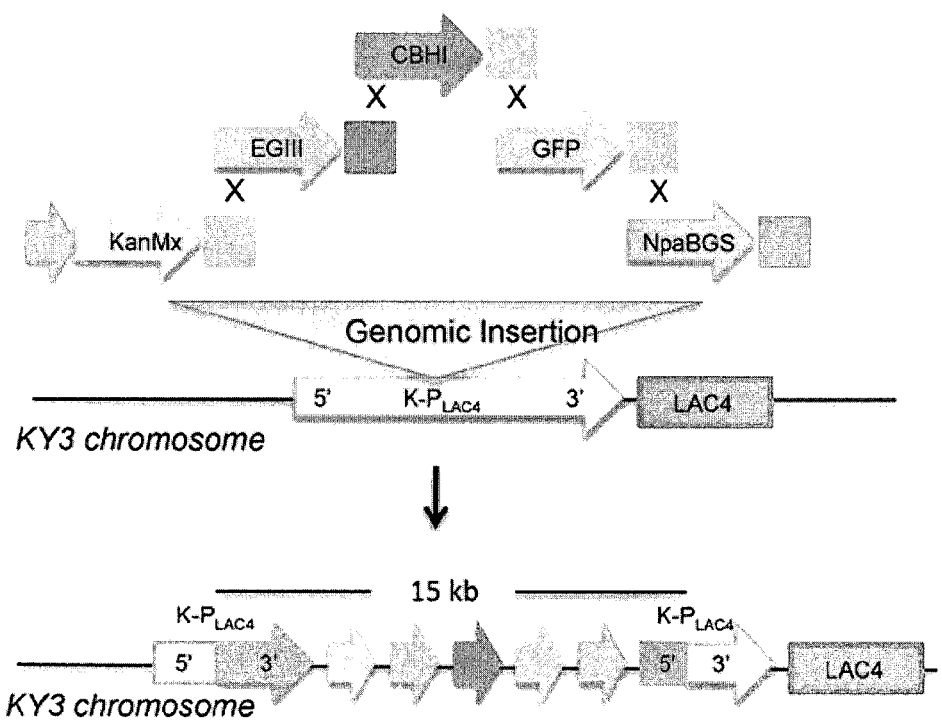

The PGASO method was used to assemble five gene cassettes into *Kluyveromyces marxianus* KY3 strain in a predesigned order. See, FIGS. 1(a) and 1(b). The resultant strain was KR5. In the first gene cassette, the kanMx gene and the *K. lactis* Lac4 promoter fragment from pKlac2 vector (*K. lactis* Protein Expression Kit, New England Biolabs) were amplified and assembled into a fragment using the Lac4-KanMx primers. The coding regions of the second and the third gene cassettes, the *T. reesei* EgIII (endoglucanase) gene and the *T. reesei* CBHI (cellobiohydrolase I) gene, were amplified from cDNA of *T. reesei* and assembled with the ScGapDH promoter and KlPADHI promoter regions by using the ScGapDH-EgIII and the KlGapDH-CBHI primer, respectively, via fusion PCR. The fourth gene cassette with the green fluorescent protein (GFP) gene was constructed using the KlADHI-GFP primers. The fifth gene cassette containing the *N. patriciarum* NpaBGS (beta-glucosidase) gene and a ScADHI promoter were respectively amplified and constructed using the ScADHI-NpaBGS primers. Each gene cassette contains a 46 bp overlapping region with its neighboring cassette on the 3' terminus for recombinatorial gene assembly. PCR was conducted using the TaKaRa Ex Taq system. The primers used are listed in Table 1 below.

TABLE 1

|  | Primer name | Sequence |
|---|---|---|
| | | Cassette construction primers |
| Lac4-KanMx | K1-PLac4-3'End-F | 5'TAGGGCCTGTTTGGCCtcccgcggggatc-3' (SEQ ID NO: 1) |
| | K1-LAC4_46bpScPGap_Dra3_R | 5'TAGCACTCAGTGATTATTTACGTATTCTTTGAAATGGCAGTATTGATAATGATAAACTTATACAACATCGAAGAAGAGTC-3' (SEQ ID NO: 2) |
| | ScPGapDH-F-BglI | 5'-TAGGCCATCACGGCAGTTTATCATTATCAATACTGCC-3' (SEQ ID NO: 3) |
| | AFEgIII_ScPGapDH_R | 5'-GTAGAGAATTTCATTTTTTTGTTTGTTTATGTGTGTTTAT-3' (SEQ ID NO: 4) |
| ScGapDH-EgIII | ScPGapDH_AFEgIII_F | 5'-ATAAACACACATAAACAAACAAAAAAATGAAATTCTCTAC-3' (SEQ ID NO: 5) |
| | ScTTGap_EgIII_R | 5'-AAGATTTAAAGTAAATTCACGCGGCCGCCTACTTTCTTGCGAGACACG-3' (SEQ ID NO: 6) |
| | EgIII_ScTTGap_F | 5'-CGTGTCTCGCAAGAAAGTAGGCGGCCGCGTGAATTTACTTTAAATCTT-3' (SEQ ID NO: 7) |
| | K1-PGapDH-F | 5'-AGTATGGTAACGACCGTACAGGCAA-3' (SEQ ID NO: 8) |
| KlGapDH-CBHI | AFCBHI_K1PGapDH_R | 5'-GTAGAGAATTTCATTTTTTTTGTGTAATATTCTTTTTTTT-3' (SEQ ID NO: 9) |
| | K1PGapDH_AFCBHI_F | 5'-AAAAAAAAGAATATTACACAAAAAAAATGAAATTCTCTAC-3' (SEQ ID NO: 10) |
| | ScTTGap_CBHI_R | 5'-AAGATTTAAAGTAAATTCACGCGGCCGCTTACAGGCACTGAGAGTAGT-3' (SEQ ID NO: 11) |
| | CBHI_ScTTGap_F | 5'-ACTACTCTCAGTGCCTGTAAGCGGCCGCGTGAATTTACTTTAAATCTT-3' (SEQ ID: NO: 12) |
| | ScTTGap_K1_PADHI_R | 5'TGGTAACGACCGTACAGGCAAGCGCGAAGGCAAATGGAAAAGCTGGTGGCGGAAAAAATTCATTTG-3' (SEQ ID NO: 13) |
| | K1-PADHI-F | 5'-CCAGCTTTTCCATTTGCCTTCGCGCTTGCC-3' (SEQ ID NO: 14) |
| K1ADHI-GFP | GFPKLADHI-R | 5'-TCCTCGCCCTTGCTCACCATTTTATCTTTTTTAGTATAGAGT-3' (SEQ ID NO: 15) |
| | KLADHIGFP-F | 5'-ACTCTATACTAAAAAAAGATAAAATGGTGAGCAAGGGCGAGGA-3' (SEQ ID NO: 16) |
| | ScTTGap_46bpScPADHI_CGA-BglI_R | 5'-TAGgccgTCGtggcATGTATGGGTTTGGTTGCCAGAAAAGAGGAAGTCCATATTGTACAC-3' (SEQ ID NO: 17) |
| | ScPADHI_CGA-BglI_F | 5'-TAGgccaCGAcggcGTGTACAATATGGACTTCCTCTTTTC-3' (SEQ ID NO: 18) |
| ScADHI-NpaBGS | NpaBGS-BglII-F | 5'-ACGAGATCTAAAAAAATGAAATTCTCT-3' (SEQ ID NO: 19) |
| | NpaBGS-SmaI-R | 5'-TATCCCGGGTTAGTAAAGTTTGTAAGC-3' (SEQ ID NO: 20) |
| | K1-PLac4-5'End-R-SfiI | 5'-AGGGCCAAGAAGGCCagccgcggaaatttaggaattttaaac-3' (SEQ ID NO: 21) |
| | ScPADHI_CGA-BglI_F | 5'-TAGgccaCGAcggcGTGTACAATATGGACTTCCTCTTTTC-3' (SEQ ID NO: 22) |

TABLE 1-continued

| Primer name | | Sequence |
|---|---|---|
| Checking primers | | |
| Kan | Kan-BglII-F | 5'-AAAAAGATCTGCCACCATGGGTAAGGAAAAGACTC-3' (SEQ ID NO: 23) |
| | Kan-XbaI-R | 5'-AAAAATCTAGATTAGAAAAACTCATCGAGCAT-3' (SEQ ID NO: 24) |
| | EgIII-1084F | 5'-GACATGTGCCAGCAAATCCAATATC-3' (SEQ ID NO: 25) |
| EgIII | ScTTGap_K1_PGapDH_R | 5'CTTTTCCATTTGCCTTCGCGCTTGCCTGTACGGTCGTTACCATACTTGGCGGAAAAAATTCATTTG-3' (SEQ ID NO: 26) |
| CBHI | K1-PGapDH-F | 5'-AGTATGGTAACGACCGTACAGGCAA-3' (SEQ ID NO: 27) |
| | CBHI-218R | 5'-AAGTGTTGCCATCGTAGCAGTTCGT-3' (SEQ ID NO: 28) |
| GFP | GFP-BglII-F | 5'-ACGAGATCTATGGTGAGCAAGGGCGA-3' (SEQ ID NO: 29) |
| | GFP-SmaI-R | 5'-TATCCCGGGTTACTTGTACAGCTCGTCCA-3' (SEQ ID NO: 30) |
| NpaBGS | NpaBGS-1422-F | 5'-TCCAGGTCCAGTTAATGTTCCATTC-3' (SEQ ID NO: 31) |
| | NpaBGS-SmaI-R | 5'-TATCCCGGGTTAGTAAAGTTTGTAAGC-3' (SEQ ID NO: 32) |
| Internal primers | | |
| amplicon-1 | Kan-673F | 5'-CAGGATCTTGCCATCCTATGGAACT-3' (SEQ ID NO: 33) |
| | EgIII-528R | 5'-TACTTGGAAATGCTCGTGGAATCAA-3' (SEQ ID NO: 34) |
| amplicon-2 | EgIII-1084F | 5'-GACATGTGCCAGCAAATCCAATATC-3' (SEQ ID NO: 35) |
| | CBHI-218R | 5'-AAGTGTTGCCATCGTAGCAGTTCGT-3' (SEQ ID NO: 36) |
| amplicon-3 | CBH-I585F | 5'-CGATCTGAAGTTCATCAATGGCCAG-3' (SEQ ID NO: 37) |
| | GFP-150R | 5'-GTGCAGATGAACTTCAGGGTCAGCT-3' (SEQ ID NO: 38) |
| amplicon-4 | GFP-492F | 5'-GAACTTCAAGATCCGCCACAACATC-3' (SEQ ID NO: 39) |
| | NpaBGS-403R | 5'-CACATTCACCAACATAGAATGGATC-3' (SEQ ID NO: 40) |

(2) Yeast Transformation and Clone Screening

The cells were incubated in 5 ml YPD medium (1% Bacto Difco-Yeast Extract, 2% Bacto Difco-Peptone, 2% Merck-D (+)-Glucose) at 30° C., shaking at 250 rpm for 16 hr. To express heterologous enzymes in KY3, a transformation method of K. lactis was employees (Colussi and Taron, 2005, Appl Environ Microbiol (71):7092-7098). The target DNA fragments in a 5 µg volume with an equal molar ratio of each fragment were mixed with 40 µl competent cells. The electroporation was performed (1.0 kV, 400Ω, and 25 µF capacitance) in BioRad system (GenePluser Xcell™, Bio-Rad, Hercules, Calif.) with an aluminum cuvette (2 mm). The cells were spread onto YPG plates (1% Bacto Difco-Yeast Extract, 2% Bacto Difco-Peptone, and 2% Merck-galactose) containing kanamycin (20 µg/mL). To confirm the presence and the desired order of each fragment, each isolated colony was digested in QucikExtract™ DNA Extraction Solution (EPICENTRE, Madison, Wis.) to remove yeast cell wall and examined by PCR with specific primer pairs. See "checking primers" in Table 1. To verify by PCR that these gene cassettes were inserted and assembled in the correct order, gene specific internal primers for each cassette were designed and used. See, Table 1. These clones were further observed under bright field microscope with phase contrast and fluorescence with a GFP filter, and photographed by a confocal microscope and single molecule detection system (Leica TCS-SP5-MP-SMD, Germany).

(3) Quantitative PCR Analysis

The cells of each isolate were incubated in YPG medium containing kanamycin (20 µg/mL) at 30° C., 200 rpm for 16 hr. The template mRNA was then purified from yeast cells using an RNeasy Protect mini kit (High Pure RNA Isolation Kit, Roche). cDNA synthesis was performed with a reverse transcription kit (SuperScript™ II kit, Invitrogen). The relative quantification of each gene was carried out via the Universal Probe Library Set (LightCycler® 480 Probes Master, Roche) with a specific primer pair (the amplicon size was 100 to 150 bp) on a LightCycler (LightCycler® 480, Roche), following the protocol of the manufacturer.

(4) Quantitative Assays of Enzyme Activities

The supernatants of yeast cultures were used in several glucanase activity assays, each with different test substrates. Total glucanase activity was assayed by mixing 40 µl supernatant of with 60 µl buffer solution (50 mM 4-methylumbelliferyl-β-D-cellobiopyranoside (MUC), 50 mM sodium acetate, pH 3). Release of 4-methylumbelliferone (MU) with fluorescence units (FU) was measured by a fluorescence intensity reader (SpectraMax M2, MDS) with the excitation at 365 nm and emission at 465 nm. Exo-glucanase and endo-glucanase activities were assayed by mixing 40 µl supernatant with 60 µl buffer solution containing either 2% phosphoric acid-swollen cellulose (PASC) or 2% CM-cellulose. The amount of reducing sugar was measured using the Somogyi-Nelson method to determine the number of glucose equivalents. The quantitative assay of β-glucosidase activity used was similar to the above method, but 50 mM p-nitrophenyl-D-glucose (pNP-Glc) was used as substrate and the detection was done with luminescence under 410 nm UV light. Protein concentration was determined by the Bradford method.

(5) Carbon Source Utilization and Ethanol Production Assay

The transformed yeast cells were grown on 2% agar YP medium plates with cellobiose, β-glycan, CMC, or PASC as carbon source individually. The same recipe in liquid medium was also used for yeast growth and ethanol fermentation. The productivity of ethanol was analyzed by gas chromatography (Shimadze GC-14, Japan) with a flame ionization detector (FID) and a stainless steel column (80/120 Carbopack B/6.6% Carbowax, 2 m×2 mm), with nitrogen as the mobile gas. The running condition included heating of the column from 80 to 150° C. at a ramp rate of 4° C. per min, an injection temperature of 180° C., and a detection temperature of 250° C. Each fermentation experiment and the subsequent analysis were repeated three times.

Results (1) Insertion of Five Gene Cassettes

To confer the hydrolysis ability of *K. marxianus* KY3 on higher order carbon sources such as cellulose, three cellulase genes, as well as a selecting marker and a reporter gene, were introduced into the KY3 genome. The three cellulase genes were a beta-glucosidase gene (NpaBGS) originally found in a cow rumen fungus, i.e., *N. patriciarum*, and two *T. reesei* cellulase genes, i.e., the EGIII and the CBHI gene. The neomycin phosphotransferase gene essential for kanamycin resistance, i.e., the KanMX gene, was used as a marker gene for clone screening. The green fluorescent protein (GFP) gene was employed as a promoter reporting system and as a biosensor to monitor cell state. The five genes were assembled as one single cassette for genetic manipulation via recombinationary insertion. To avoid unexpected recombination events in multi-gene integration into similar regions, various heterologous promoters with low homologous sequences were used. An ideal promoter preferably have certain properties, e.g., high strength, low background, rapid induction, and simple induction conditions. Several constitutive promoters that fulfill these conditions were chosen for the five-gene cassettes. These promoters included ScPGapDH (the GapDHI promoter) and ScPADHI (the AdhI promoter) from *S. cerevisiae*, and KlPGapDH and KlPADHI from *K. lactis*, which showed only 40-55% sequence identity between each other in the 5' upstream region.

Transformation of five gene cassettes in a single step into the genome of *K. marxianus* KY3 was achieved. The first gene cassette included a selection marker gene (the KanMX gene, 810 bp) linked with a portion of the PLac4 promoter. In the second gene cassette, an endoglucanase gene (the EGIII gene, 1449 bp) was linked with the KlPGapDH promoter. An exoglucanase gene (the CBHI gene, 1749 bp) driven by the KlPGapDH promoter was used in the third gene cassette. The fourth gene cassette contained a reporter gene (the GFP gene, 720 bp) as well as the ScPADHI promoter. In the last gene cassette, a beta-glucosidase gene (the NpaBGS gene, 2526 bp) was linked with the KlPADHI promoter. These five gene cassettes were prepared by PCR, with a 46 bp overhang to the 5' end of each promoter and a 46 bp overhang to the 3' end of the terminator region. See, FIG. 1(a).

The overhangs were designed to facilitate homologous recombination, because the 5' end of each fragment overlaps with the 3' end of its 5' upstream neighbor; the 5' overhang of the first cassette (the KanMX gene) and the 3' terminal on the last cassette (the NpaBGS gene) overlap with the LAC4 promoter region in *K. marxianus* KY3. See, FIG. 1(b). Consequently, the five gene cassettes, each with an independent promoter, alpha factor from *K. lactis*, gene coding region, and a terminator, were assembled in the predesigned order, i.e., Kan-EGIII-CBHI-GFP-NpaBG, as a 14877 by DNA fragment. The fragment was integrated into the LAC4 promoter region of *K. marxianus* KR3 via single-step genome recombination, resulting in strain KR5. See, FIG. 1(b). Strain KR5 was selected with kanamycin resistance. The activation of green fluorescent protein via promoter ScPADHI was confirmed by fluorescence microscopy.

The five-gene insertion in KR5 was confirmed by PCR with five pairs of gene specific internal primers (see Table 1). To verify that these gene cassettes were assembled in the correct order, four internal primer pairs spanning the gap regions of each cassette were designed (see Table 1) and used in PCR. The one-step multi-gene fragment assembly method has thus been successfully demonstrated in KR5.

Figure 2A:
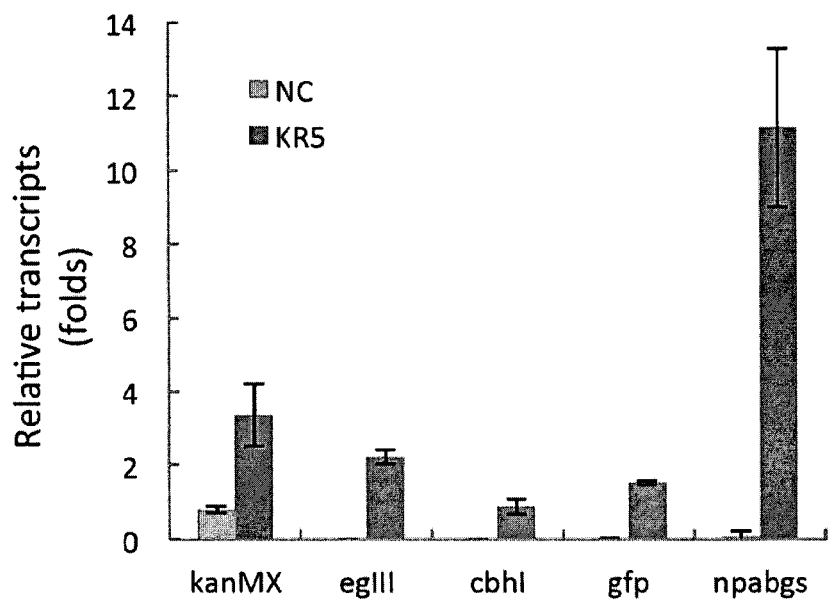
FIGS. 2(a) and (b) are bar graphs showing (a) the relative ratios of the transcripts of various genes and (b) the copy numbers of the genes in K. marxianus strains NC and KR5.
Figure 2B:
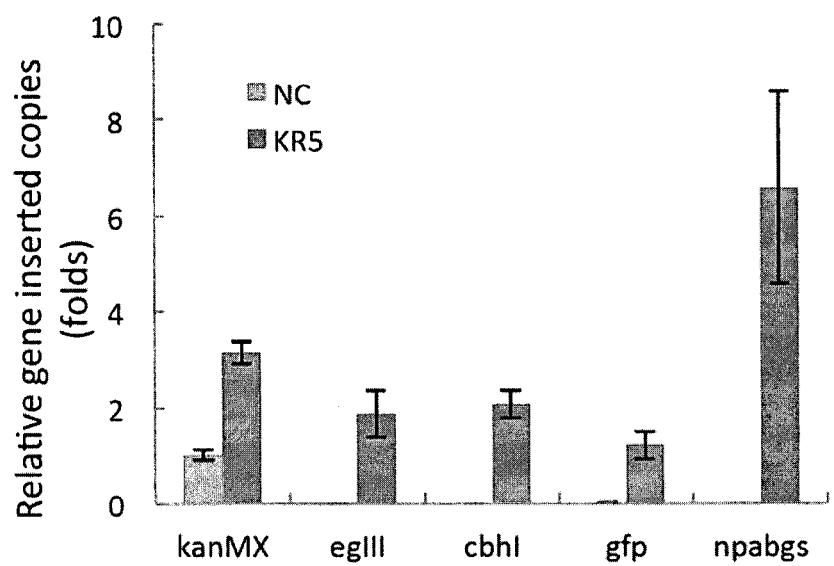

In addition, genomic DNA and total RNA were isolated from KR5 and the control strain NC (KY3 transformed with a vector containing the KanMX gene) for quantitative PCR analysis, which was performed with 5 gene-specific primer sets using the UPL system. The relative gene expression levels of the five genes in KR5 were about 3 (kan), 2 (egIII), 1 (cbhI), 1.5 (gfp) and 11 (NpaBGS) folds higher relative to the expression level of actin. See, FIG. 2(a). Similarly, the observed inserted copy number ratios of the five genes in the isolates relative to the endogenous actin gene were approximately 3 (kan), 2 (egIII), 2 (cbhI), 1.5 (gfp) and 6 (NpaBGS). See, FIG. 2(b). The data indicated unequal gene copy numbers and transcript abundances among the five genes. The differences might have been caused by non-specific gene insertions and varying transcription efficiencies among different promoters. A comparison of the transcript abundances with the inserted copy numbers suggests that, in KR5, the GapDHI promoter from *K. lactis* was weakest and the AdhI promoter from *S. cerevisiae* was the strongest promoters among the constitutive promoters used in this study.

All promoters used here were derived from strong constitutive genes associated with yeast-specific metabolic pathways. The use of this type of promoter is advantageous, as the engineered strains can be driven under normal growth, on different carbon sources, or under a high cell density immobilization condition. Moreover, the wide spectrum of induction strengths observed in different promoters may be drawn upon to devise efficient gene expression systems for optimal enzyme-cocktails or to study gene regulation in yeast.

This study shows that assembling specific sequences using over-lapping fragments is feasible and that PSOGA can be tailored for various purposes via promoter design. It also shows that KY3 is a great host for multi-gene assembly and genome engineering via synthetic biology.

(2) Characterization of the Secreted Cellulases of KR5

To quantify the secreted cellulase activities, the supernatant of KR5 was harvested for analysis without protein purification. The commercial cellulolytic enzyme mixture kits Celluclase 1.5L and Noval88 were used as benchmarks. The supernatant with KR5 secreted cellulases and diluted commercial enzymes were estimated using an equal MUC activity which represented the total glucanase activity.

Figure 3A:
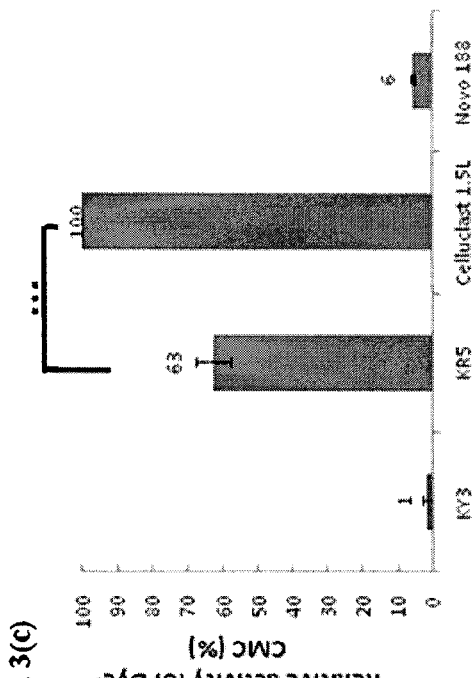
FIGS. 3(a)-3(d) are bar graphs showing the cellulolytic enzyme activities in the supernatant of KR5 culture as compared to those of K. marxianus strain KY3 and commercial cellulolytic enzyme mixture kits, i.e., Celluclast 1.5 L and Novozyme 188. The relative activities were assessed using (a) MUC, (b) Dye-CMC, (c) PASC, and (d) pNPG as the substrate, respectively. The protein concentration in the supernatant of the K. marxianus cultures was 1.3 mg/ml. *: P<0.05 (significant), : P<0.01; *: P<0.001; N.S., non-significant.
Figure 3C:
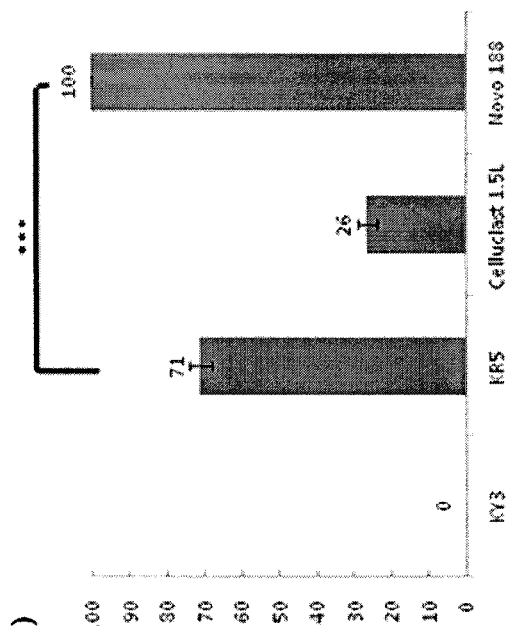
Figure 3B:
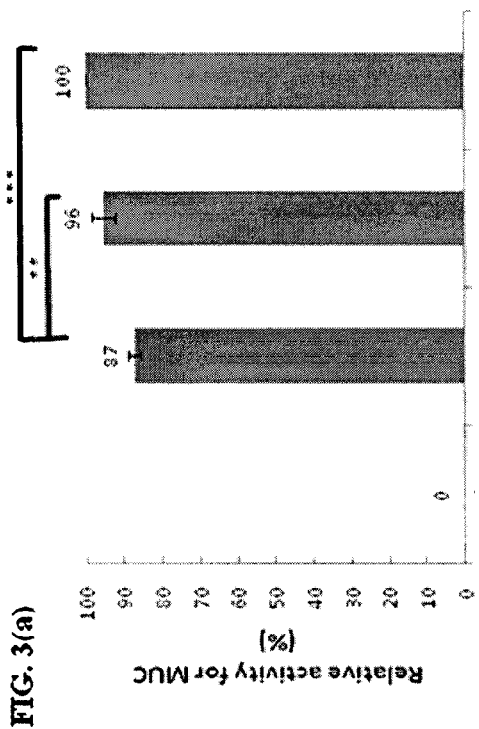
Figure 3D:
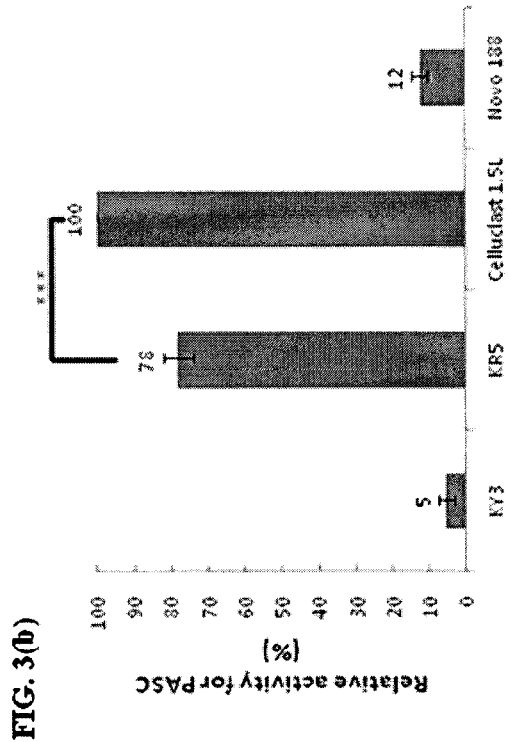

The MUC activity assay was performed with MUC as the substrate, and the results indicated that the MUC activity in the supernatant of KR5 was equivalent to those of 0.5 unit of Celluclast 1.5 L and 1 unit of Novozyme 188, and higher than that of the control strain (i.e., KY3). See, FIG. 3(a). The glucose assay indicated significantly improved digestion of PASC by KR5; the activity was up to 80% of that of the 0.5 unit of Celluclast 1.5 L. See, FIG. 3(b). The activity assay with Dye-CMC as the substrate suggested that the endoglucanase activity in the supernatant of KR5 was significantly improved due to the EGIII secreted by KR5; the activity was 60% of the 0.5 unit of Celluclast 1.5 L. See, FIG. 3(c). The activity assay with pNPG as the substrate showed that the beta-glucosidase activity of NpaBGS in the supernatant of KR5 was higher than that of the control strain, and the activity was nearly 80% of 1 unit of Novozyme 188. See, FIG. 3(d). These data demonstrate successful co-expression of the exogenous fungal genes and secretion of their gene products without any significant post-translational modification problems.

Successful protein production in a heterologous host at a commercial scale often requires the regulation of the timing and the expression level of the cloned gene(s). The long culturing time required by fungi is a current bottleneck of traditional enzyme purification technologies, such as Celluclast 1.5 L for *Trichoderma* and Novol88 for *Aspergillus*. The faster growth rate of *K. marxianus* makes it more desirable for commercial applications. In this study, the promoters described above and the signal sequence of the *K. lactis* alpha-mating factor were used to express and secret heterologous cellulases in KR5, at a much higher efficiency than the classical *S. cerevisiae* system. Furthermore, the new host strain *K. marxianus* KR5 is not only naturally competent to secrete enzymes, but also efficient for combining different enzyme systems for downstream processing of industrial enzymes.

(3) Sugar Utilization and Ethanol Production of KR5

Figure 4A:
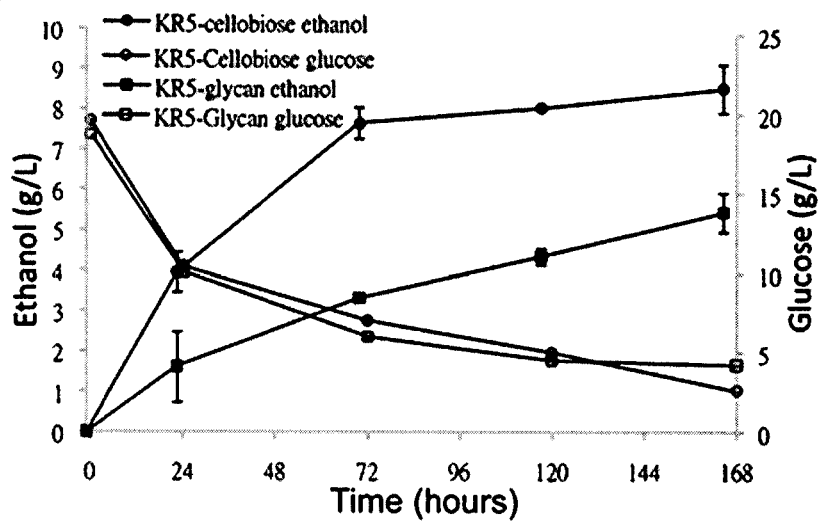
FIGS. 4(a) and 4(b) are graphs showing the fermentation ability of KR5.
Figure 4B:
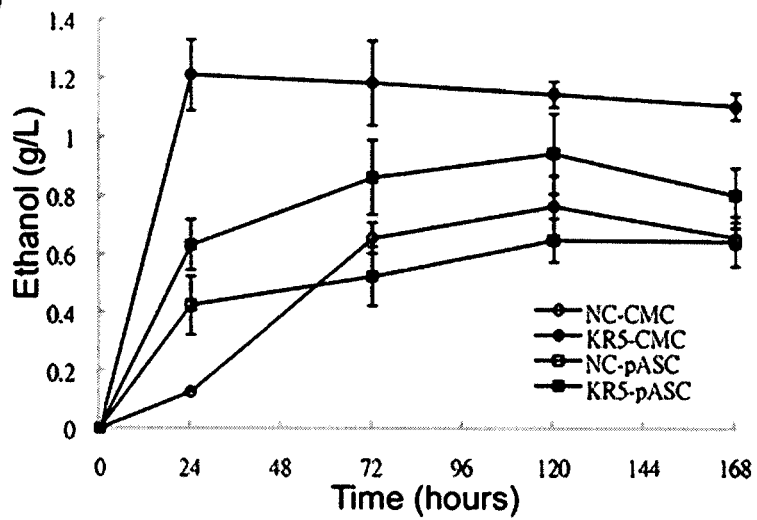

Several types of cellulose were tested in this study to determine the carbon source utilization and ethanol fermentation abilities of KR5, KY3-196, which is a KY3 strain transformed with the NpaBGS gene, and the control strain NC. All three strains were capable of utilizing glucose and cellobiose for growth, but only KR5 can, additionally, assimilate beta-glycan and CMC. To examine the SSF ability of KR5, fermentation was performed in YP medium containing cellobiose, beta-glycan, CMC, or PASC as the sole carbon source. After cultivation of cells in YPD medium for 24 h at 30° C., the cells with O.D. 20 were harvested for subsequent inoculums. KR5 could use cellobiose, beta-glycan, CMC or PASC as the sole carbon source for fermentation. The efficiency of cellobiose conversion with KR5 was as good as its glucose utilization, where it produced 8.5 g/L ethanol with a 93% conversion ratio in 168 h at 37° C. See, FIG. 4(a). When 2% beta-glycan was the sole carbon source, KR5 produced 5.4 g/L ethanol with a 74% conversion ratio in 168 h at 37° C. See, FIG. 4(a). These data indicated that KR5 could express cellulolytic enzymes and directly produce ethanol from cellulosic materials. The CMC and PASC assimilation abilities were only moderately increased compared to the control strain. See, FIG. 4(b).

Example 2

Insertion of Seven Gene Cassettes

Figure 5:
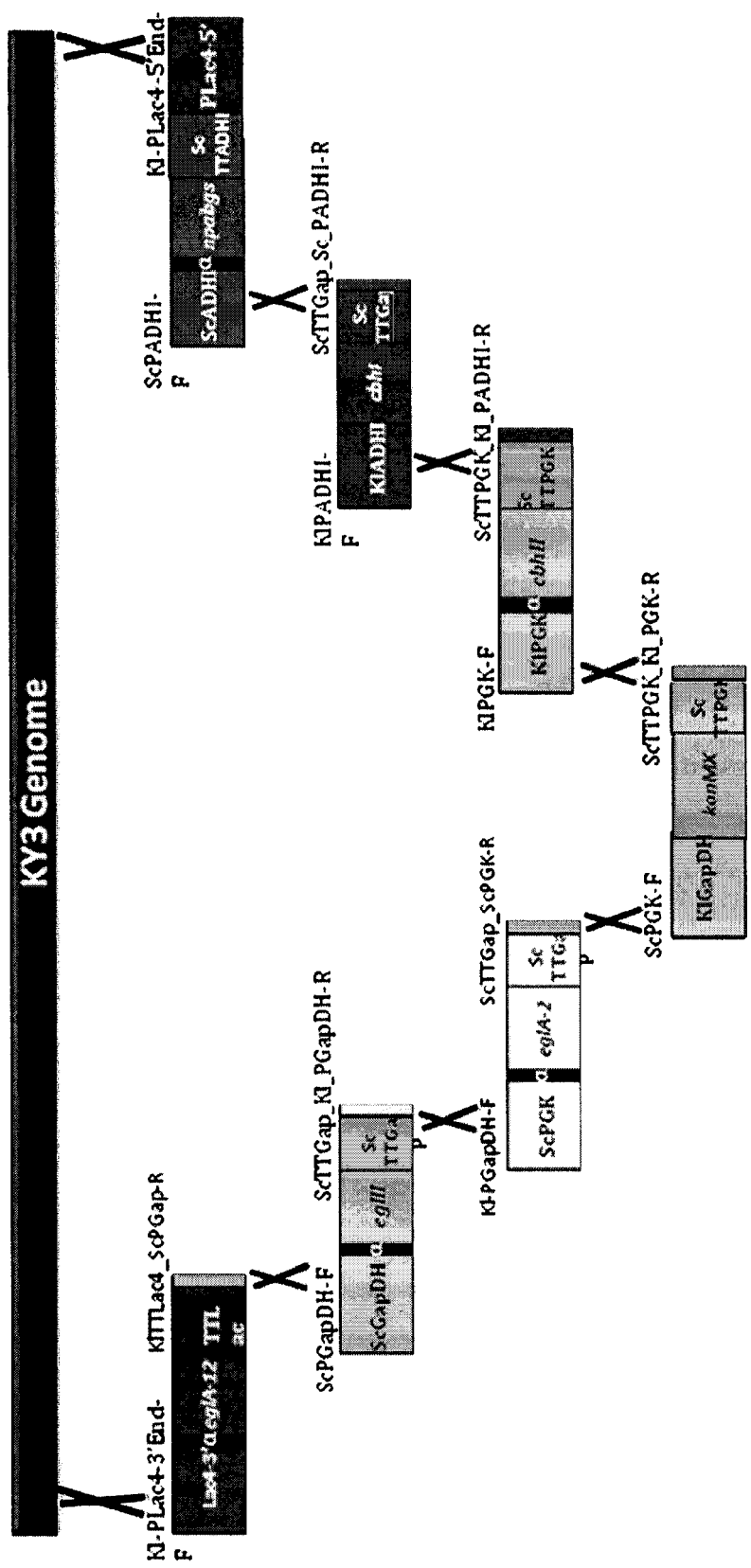
FIG. 5 is a schematic diagram showing exemplary gene cassettes and the genomic integration of 7 gene cassettes in strain KR7+.

The PGASO method was used to assemble into KY3 in a predetermined order six cellulase genes, i.e., cbhIII from *T. reesei* (encoding a 1,4-beta-D-glucan), cbhI from *T. reesei*, egIII from *T. reesei*, eglA-2 from *A. niger* (encoding an endoglucanase), eglA-12 (encoding an endoglucanase) from *A. niger*, and npabgs from *N. patriciarum*, plus a selection marker gene, kanMX The seven gene cassettes, with a total length of ~2 Kb, were constructed in the predesignated order of eglA-12, egIII, eglA-2, kanMX, cbhII, cbhI, and npabgs; the promoter driving the genes were KlLac4, ScGapDH, ScPGK, KlGapDH, KlPGK, KlADHI, and ScADHI, respectively. See FIG. 5. The resultant strain was named KR7$^+$.

The brown-rot fungus *T. reesei* simultaneously expresses three kinds of endo-β-1,4-glucanases. The major one is endoglucanase III (EGIII) when treated with a barley straw substrate. The gene product of egIII (Accession No. M19373.1), with 418 amino acids, contains a CBM 1 (cellulose binding domain) and a GH5 catalytic domain. *A. niger* can secret two types of endoglucanase A (EglA), i.e., EglA-2 and EglA-12, belong to the GH2 family and GH12 the family, respectively. The gene product of eglA-2 (Accession No. XM_001397945.2), with 517 amino acids, also contains a CBM-1 and a GH2 catalytic domain. The gene product of eglA-12 (Accession No. GU724764.1) has only 239 amino acids and contains a GH12 catalytic domain.

Compared to another strain, the KR7 strain, the CBHI gene in KR7$^+$ was linked to a stronger promoter, KlADHI, instead of the lowest strength promoter, KlGapDH, to increase the cellobiohydrolase productivity in KR7$^+$. In addition, in KR7, the selection marker gene was driven by the strongest promoter, KlLac4, and was located at one terminus of the seven gene cassettes.

In constructing KR7, a low transformation accuracy of the gene cassettes was observed. As compared to KR7, the transformation accuracy in constructing KR7$^+$ was increased 2.6 folds, and an average of 8% colonies were found to have the correct assembly of the cassettes in the predesigned order. These observations suggest that the promoter strength and the location of the selection marker gene can be two important factors in the formulation of a cellulase cocktail.

Figure 6A:
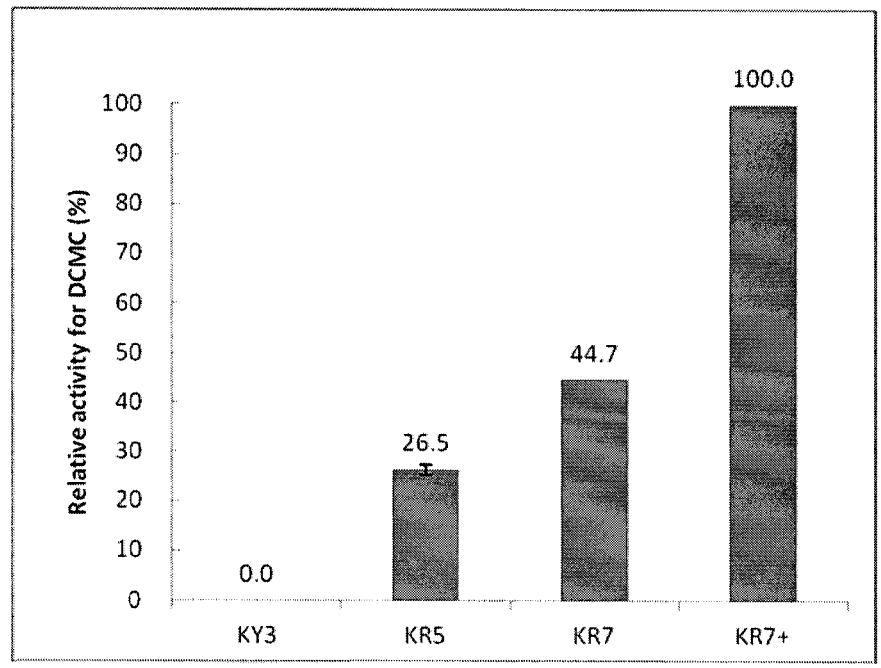
FIGS. 6(a)-6(d) are bar graphs showing the cellulolytic enzyme activities in the supernatant of KR7+ culture.
Figure 6B:
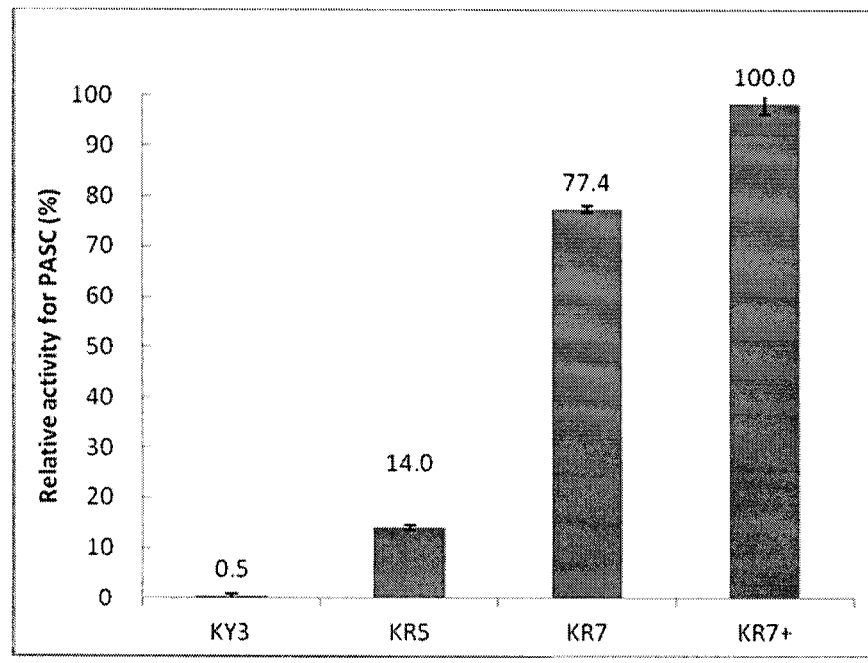
Figure 6C:
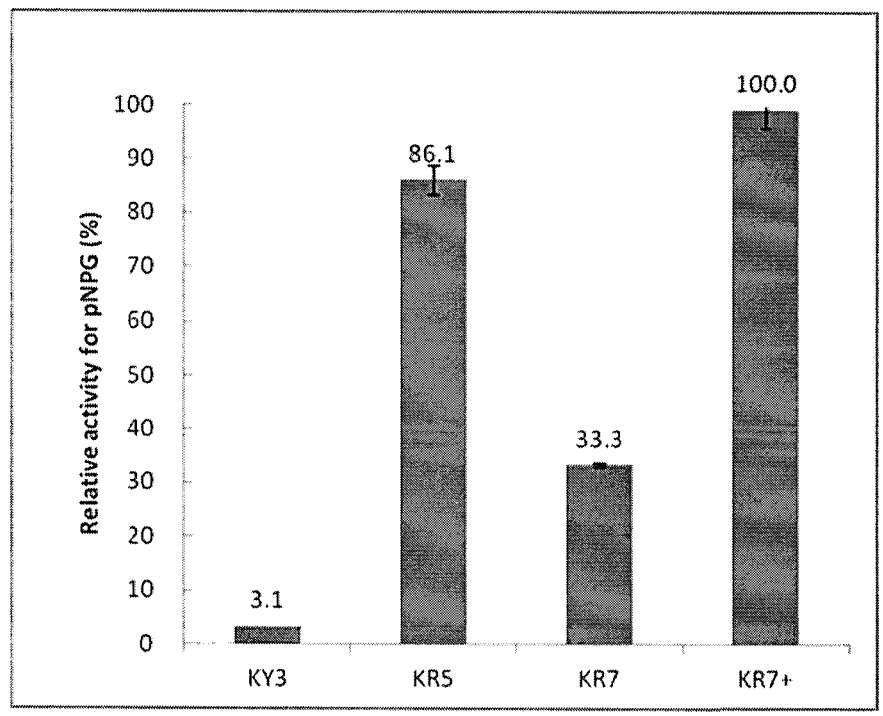
Figure 6D:
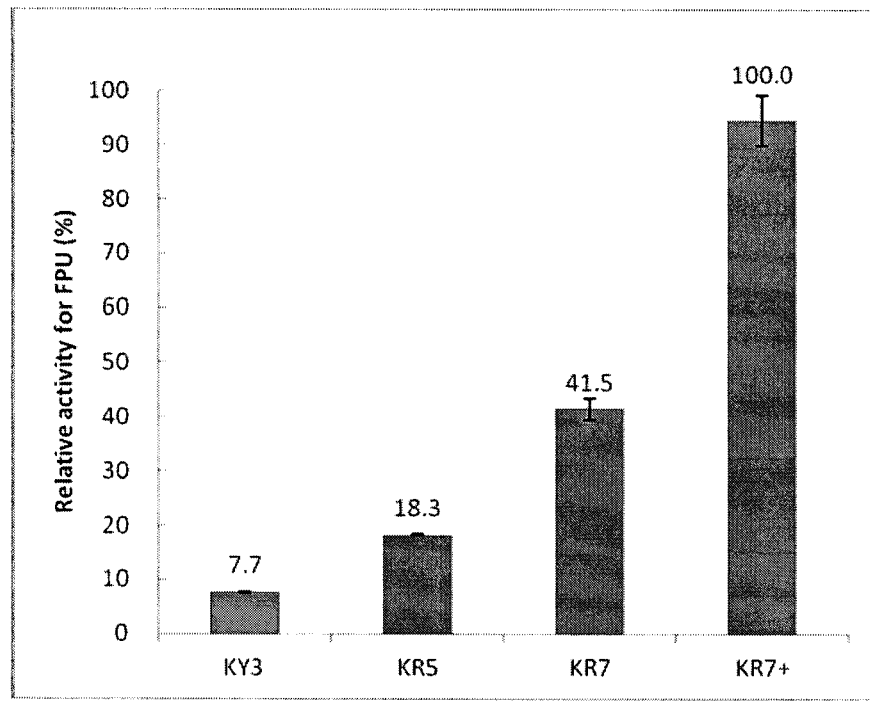

To quantify the activities of secreted cellulases, the supernatants of KY3, KR5, KR7 and KR7$^+$ cultures were harvested and concentrated for analysis at 40° C. Data from relative activity assay with Dye-CMC as the substrate showed that the endo-β-1,4-glucanase activity in the supernatant of KR7$^+$ was 2.3 times higher than that of KR7, probably due to the additional EglA-12 gene. See, FIG. 6(a). The relative activity with PASC showed that the supernatant of KR7$^+$ had a 1.2-fold improvement over KR7, probably due to the slight increase in the expression level of CBHI in KR7$^+$. See, FIG. 6(b). The relative activity of beta-glucosidase in the supernatant of KR7 was decreased, but the supernatant of KR7$^+$ displayed a higher beta-glucosidase activity than those of KR5 and KR7. See, FIG. 6(c). The overall cellulase activity assay was conducted using the filter paper assay (FPA), and the supernatant of KR7$^+$ showed a 2.4-fold and a 5.5-fold improvement in the FPA activity over those of KR7 and KR5, respectively. See, FIG. 6(d). These data showed that the new strain, KR7$^+$, was capable of co-expressing 6 different cellulases, and the secretion of their gene products displayed a synergistic effect on cellulolytic enzyme activities. It also showed that a desired co-expression profile can be achieved by promoter rearrangement and gene cassette replacement strategies in a yeast host.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of inserting a plurality of nucleic acid molecules in a predetermined order into a predetermined site in the genome of a cell, the method comprising, providing a plurality of nucleic acid molecules to be inserted into a predetermined site in the genome of the cell in a predetermined order next to each other, the plurality of nucleic acid molecules including a first nucleic acid molecule in the order, a last nucleic acid molecule in the order and at least one intervening nucleic acid molecule to be inserted between the first and last nucleic acid molecules, wherein each of the plurality of nucleic acid molecules contains (a) a nucleic acid sequence operatively linked to a promoter sequence at the 5' end of the nucleic acid molecule, and (b) an overlapping sequence at the 3' end of the nucleic acid molecule, the promoter sequence in each nucleic acid molecule being different, wherein the overlapping sequence in the at least one intervening nucleic acid molecule is homologous to a portion of a promoter sequence in an adjacent nucleic acid molecule and a portion of the promoter sequence in the at least one intervening nucleic acid molecule is homologous to the overlapping sequence in another adjacent nucleic acid molecule, and wherein a portion of the promoter sequence of the first nucleic acid molecule is homologous to a first sequence in the predetermined site and the overlapping sequence of the last nucleic acid molecule is homologous to a second sequence in the predetermined site; and introducing the plurality of nucleic acid molecules simultaneously into the cell, whereby the plurality of nucleic acid molecules join together in the predetermined order via homologous recombination between the overlapping sequences and the promoter sequences, and are inserted into the genome via homologous recombination between the promoter sequence of the first nucleic acid molecule and the first sequence in the predetermined site and between the overlapping sequence of the last nucleic acid molecule and the second sequence in the predetermined site.

2. The method of claim 1, wherein the each promoter sequence includes a promoter and a 5' upstream sequence of the promoter.

3. The method of claim 2, wherein the portion of the promoter sequence that is homologous to an overlapping sequence or a sequence in the predetermined site includes the 5' upstream sequence.

4. The method of claim 1, wherein the predetermined site is a promoter region.

5. The method of claim 1, wherein the predetermined site is a group of sequence repeats.

6. The method of claim 1, wherein the predetermined site is an exogenous sequence inserted into the genome of the cell.

7. The method of claim 1, wherein the plurality of nucleic acid molecules include at least five nucleic acid molecules.

8. The method of claim 1, wherein the nucleic acid sequences in the plurality of nucleic acid molecules respectively encode a selectable marker, a reporter protein, and at least one enzyme.

9. The method of claim 8, wherein the enzyme is selected from the group consisting of a beta-glucosidase, an endoglucanase, an exoglucanase, a cellubiohyrolase, a protease, a nuclease, an amylase, a laccases, a pectinase, a lipase, and a peptide.

10. The method of claim 1, wherein the promoter sequence in each of the plurality of nucleic acid molecules includes a *K. lactis* Lac4 promoter, a *S. cerevisiae* GapDHI promoter, a *K. lactis* GapDHI promoter, a *S. cerevisiae* AdhI promoter, a *S. cerevisiae* PGK promoter, a *K. lactis* PGK promoter, or a *K. lactis* AdhI promoter.

11. The method of claim 1, wherein the nucleic acid sequence in each of the plurality of nucleic acid molecules includes the *A. niger* eglA-12 gene, the *T. reesei* egIII gene, the *A. niger* eglA-2 gene, the KanMx gene, the *N. patriciarum* npabgs gene, the *T. reesei* cbhI gene, or the *T. reesei* cbhII gene.

12. The method of claim 1, wherein the cell is a *Kluyveromyces marxianus*.

13. The method of claim 12, wherein the plurality of nucleic acid molecules includes (1) a first nucleic acid molecule that contains the *K. lactis* Lac4 promoter operably linked to the KanMx gene, (2) a first intervening nucleic acid molecule that contains the *S. cerevisiae* GapDHI promoter operably linked to the *T. reesei* egIII gene, (3) a second intervening nucleic acid molecule that contains the *K. lactis* GapDHI promoter operably linked to the *T. reesei* cbhI gene, (4) a third intervening nucleic acid molecule that contains the *K. lactis* AdhI promoter operably linked to the green fluorescent protein gene, and (5) a last nucleic acid molecule that contains the *S. cerevisiae* AdhI promoter operably linked to the *N. patriciarum* npabgs gene, wherein the plurality of nucleic acid molecules are designed to be integrated into the genome of the cell in the order of (1)-(2)-(3)-(4)-(5) in the 5' to 3' direction.

14. The method of claim 11, wherein the plurality of nucleic acid molecules includes (1) a first nucleic acid molecule that contains the *K. lactis* Lac4 promoter operably linked to the *A. niger* eglA-12 gene, (2) a first intervening nucleic acid molecule that contains the *S. cerevisiae* GapDHI promoter operably linked to the *T. reesei* egIII gene, (3) a second intervening nucleic acid molecule that contains the *S. cerevisiae* PGK promoter operably linked to the *A. niger* eglA-2 gene, (4) a third intervening nucleic acid molecule that contains the *K. lactis* GapDHI promoter operably linked to the kanMx gene, (5) a fourth intervening nucleic acid molecule that contains the *K. lactis* PGK promoter operably linked to the *T. reesei* cbhII gene, (6) a fifth intervening nucleic acid molecule that contains the *K. lactis* AdhI promoter operably linked to the *T. reesei* cbhI gene, and (7) a last nucleic acid molecule that contains the *S. cerevisiae* AdhI promoter operably linked to the *N. patriciarum* npabgs gene, wherein the plurality of nucleic acid molecules are designed to be integrated into the genome of the cell in the order of (1)-(2)-(3)-(4)-(5)-(6)-(7) in the 5' to 3' direction.

15. The method of claim 1, wherein the homologous portion between an overlapping sequence and a promoter sequence, the homologous portion between a promoter sequence and a predetermined site, and the homologous portion between an overlapping sequence and a predetermined site are each 40-60 bases long.

16. The method of claim 15, wherein the homologous portions in the promoter sequences share 50% or less sequence identity with each other.

17. The method of claim 1, wherein the nucleic acid sequences in the plurality of nucleic acid molecules respectively encode a selectable marker and at least one enzyme.

\* \* \* \* \*